(12) United States Patent
Maher et al.

(10) Patent No.: US 9,486,354 B2
(45) Date of Patent: Nov. 8, 2016

(54) CERVICAL COLLAR

(71) Applicants: Robert Michael Maher, Columbus, OH (US); Michael Paloian, Cold Spring Harbor, NY (US)

(72) Inventors: Robert Michael Maher, Columbus, OH (US); Michael Paloian, Cold Spring Harbor, NY (US)

(73) Assignee: NEURORESCUE, LLC, New Albany, OH (US)

( * ) Notice: Subject to any disclaimer, the term of this patent is extended or adjusted under 35 U.S.C. 154(b) by 449 days.

(21) Appl. No.: 14/052,346

(22) Filed: Oct. 11, 2013

(65) Prior Publication Data

US 2014/0039365 A1    Feb. 6, 2014

Related U.S. Application Data

(63) Continuation-in-part of application No. 13/309,173, filed on Dec. 1, 2011, now abandoned.

(60) Provisional application No. 61/419,018, filed on Dec. 2, 2010.

(51) Int. Cl.
| | |
|---|---|
| *A61B 5/01* | (2006.01) |
| *A61F 7/00* | (2006.01) |
| *A61F 5/055* | (2006.01) |
| *A61B 5/00* | (2006.01) |
| *A61F 7/10* | (2006.01) |
| *A61F 7/02* | (2006.01) |

(52) U.S. Cl.
CPC .............. *A61F 7/0085* (2013.01); *A61B 5/01* (2013.01); *A61B 5/6812* (2013.01); *A61F 5/055* (2013.01); *A61F 7/10* (2013.01); *A61B 5/4836* (2013.01); *A61B 5/6822* (2013.01); *A61F 7/106* (2013.01); *A61F 2007/0009* (2013.01); *A61F 2007/0011* (2013.01); *A61F 2007/0056* (2013.01); *A61F 2007/0086* (2013.01); *A61F 2007/0228* (2013.01); *A61F 2007/0231* (2013.01)

(58) Field of Classification Search
CPC ..................................................... A61F 7/0085
USPC ...... 602/14, 5, 1, 2, 18, 41, 60, 61; 607/109, 607/108, 96, 1, 104, 105
See application file for complete search history.

(56) References Cited

U.S. PATENT DOCUMENTS

| | | |
|---|---|---|
| 2,250,840 A | 7/1941 | Pomeranz |
| 4,745,922 A | 5/1988 | Taylor |
| 4,821,354 A | 4/1989 | Little |
| 4,886,063 A | 12/1989 | Crews |
| 5,072,875 A * | 12/1991 | Zacoi ......................... A61F 7/02 607/104 |
| 5,211,623 A | 5/1993 | Sarkozi |
| 5,415,624 A | 5/1995 | Williams |

(Continued)

OTHER PUBLICATIONS

International Search Report, Patent Cooperation Treaty, Completed Feb. 27, 2012, mailed Mar. 9, 2012, 11 Pages.

*Primary Examiner* — Tarla Patel
(74) *Attorney, Agent, or Firm* — Walter | Haverfield LLP; James J. Pingor (57) ABSTRACT

A cervical collar that facilitates therapeutic hypothermia is provided and includes an outer shell having a front portion and a back portion fixedly coupled to the front portion on one side and removably coupled to the front portion on an opposite side. A fastening device removably couples the back portion to the front portion on the opposite side. At least one cooling device is provided on an interior of the outer shell to induce hypothermia in a patient. A sensor is provided that measures a physical characteristic of the patient.

19 Claims, 9 Drawing Sheets

(56) References Cited

U.S. PATENT DOCUMENTS

| | | |
|---|---|---|
| 5,449,379 A | 9/1995 | Hadtke |
| 5,871,526 A * | 2/1999 | Gibbs .................. A61F 7/02 165/46 |
| 6,152,953 A * | 11/2000 | Hipskind ............... A61F 7/10 607/109 |
| 6,183,501 B1 | 2/2001 | Latham |
| 6,561,995 B1 | 5/2003 | Thibodo |
| 6,602,213 B1 | 8/2003 | Figley |
| 6,840,955 B2 | 1/2005 | Ein |
| 7,785,359 B2 | 8/2010 | Latham |
| 7,846,118 B2 | 12/2010 | Sandhu |
| 7,861,326 B2 * | 1/2011 | Harty ............... A41D 13/0512 2/468 |
| 2003/0236561 A1 | 12/2003 | Lennox |
| 2005/0284416 A1 * | 12/2005 | Smit .................. A01K 13/006 119/850 |
| 2006/0079820 A1 * | 4/2006 | Sandhu ............... A61F 5/055 602/18 |
| 2008/0269852 A1 * | 10/2008 | Lennox ................ A61F 7/02 607/104 |
| 2010/0305669 A1 | 12/2010 | Sasaki |
| 2011/0054577 A1 | 3/2011 | Latham |
| 2013/0030341 A1 * | 1/2013 | Freer ............... A61F 13/0233 602/43 |
| 2014/0128945 A1 * | 5/2014 | Schoning ............ A61F 7/106 607/109 |

\* cited by examiner

CERVICAL COLLAR

CROSS-REFERENCE TO RELATED APPLICATIONS

This application is a Continuation-in-Part of pending U.S. patent application Ser. No. 13/309,173 entitled "CERVICAL COLLAR" filed Dec. 1, 2011, which claims the benefit of U.S. Provisional Patent application Ser. No. 61/419,018 entitled "CERVICAL COLLAR" filed on Dec. 2, 2010. The entirety of the above-noted applications is incorporated herein by reference.

ORIGIN

The innovation disclosed herein relates to a cervical collar and more particularly to a cervical collar employing a cooling device for therapeutic hypothermia.

BACKGROUND

A "neck brace" or "cervical collar" is a medical, and more particularly an orthopedic, device that is often used to support the cervical portion of a patient's spinal cord by immobilizing the head and neck region. These devices are often used by emergency medical technicians (EMTs), for example when responding to victims of traumatic head or neck injuries. Other uses of the devices include treatment of chronic medical conditions, sports injuries or the like.

Traumatic head or neck injury can expose a patient to extensive spinal cord injury which could escalate to full or partial paralysis, or even death. In an effort to minimize these risks and to stabilize the top vertebrae, EMTs, and other medical personnel, often position a cervical collar on patients as a precautionary measure. Additional stabilization methods can be accomplished by way of other devices such as a backboard. Other uses of the cervical collar are for treatment of injuries including, strains, sprains or whiplash.

The innovation disclosed herein is an improvement to the conventional cervical collars described above.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a cervical collar that facilitates therapeutic hypothermia. The cervical collar includes an outer shell having a front portion and a back portion fixedly coupled to the front portion on one side and removably coupled to the front portion on an opposite side. A fastening device removably couples the back portion to the front portion on the opposite side. At least one cooling device disposed on an interior of the outer shell to induce hypothermia in a patient. A sensor that measures a physical characteristic of the patient.

In accordance with another aspect of the innovation, a cervical collar is provided that includes an outer shell, a fastening device that removably couples opposite ends of the outer shell, at least one cooling chamber configured to hold a cooling fluid disposed on an interior of the outer shell, and an indicator that measures a temperature of the cooling fluid.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. Moreover, not all illustrated acts may be required to implement a methodology in accordance with the innovation.

Following is a discussion of the innovation and some example applications of the features, functions and benefits of employing a stabilizing device having a cooling device as described herein. The innovation, in a broad application, is directed to the concept of induced or therapeutic hypothermia. Therapeutic hypothermia is a medical treatment for lowering one's core temperature to, for example, around 33° Celsius or other target temperature. Therapeutic hypothermia can be used to reduce the risk of tissue injury due to a period of insufficient blood flow caused by, for example, cardiac arrest or the occlusion of an artery by an embolism, as often occurs in the case of strokes. Studies have demonstrated, as is appreciated by those knowledgeable in the art that patients at risk for ischemic brain injuries have better results if treated with therapeutic hypothermia within the first sixty minutes after the traumatic event.

Therapeutic hypothermia may be induced by either invasive or non-invasive procedures. Some non-invasive procedures may include packing or placing cold packs, cold compresses in the axil area, under the armpits or in the groin area to try to cool blood vessels. Another non-invasive procedure includes placing a chilled water blanket or torso vest and/or leg wraps in direct contact with the patient's skin. Some invasive procedures may include administering approximately 2,000 ccs (two bags) of a normal chilled saline solution, often referred to as a crystalloid, or placing a catheter in the inferior vena cava via the femoral vein.

The innovation disclosed herein enables pre-hospital care providers to get a thorough jumpstart of inducing therapeutic hypothermia through a non-invasive procedure. As used herein, pre-hospital care providers can include care administered by EMTs, paramedics, army medics, sports trainers, etc. In other words, the innovation can be employed by most anyone in the field. Similarly, the features, functions and benefits can be employed in a hospital or other medical care facility without departing from the spirit and/or scope of the innovation described herein.

While the innovation and the example embodiments described herein are directed to a cervical collar that includes a cooling device to target the carotid artery, it is to be appreciated that the features, functions and benefits of the innovation can be applied to other regions of the body for cooling. Essentially, most any region whereby blood flows and can be affected by the cooling device of the stabilizing device. For instance, areas where pulse points are located are most often good candidate regions for placement of the innovation. For example, in addition to the spinal/neck region, the innovation can be employed in the axil area or the groin area. As will be understood, in order to enhance effects of cooling, it is important to cool as much blood as possible, thus, highly vascular regions are key regions for implementation, e.g., jugular veins, carotid arteries.

In accordance with some aspects of the innovation, the innovation facilitates the placement of the cooling device in strategic anatomical positions on the neck region. Thus, the cooling device of the cervical collar can target the carotid arteries, which supplies the supply of blood flow to the brain, in the interior portion of the neck. In other aspects, the cooling device can target the posterior portion of the neck to cool the cervical areas of the neck to decrease swelling around the posterior portion of the neck including the spinal cord area and essentially cooling the neck as a whole. Thus, the cervical collar is capable of decreasing the temperature of the blood in highly vascular regions so as to enhance induced hypothermic reaction. More specifically, the cervical collar can selectively cool the cerebral vasculature relative to the whole body thereby inducing hypothermia. Because the cooling effect to the patient is targeted to a specific area (e.g., the brain), any side effects associated with whole body cooling are significantly reduced. Effectively, the cervical collar can most often be employed in three primary scenarios, stroke, heart attack, and head/neck injury or trauma.

Figure 1:
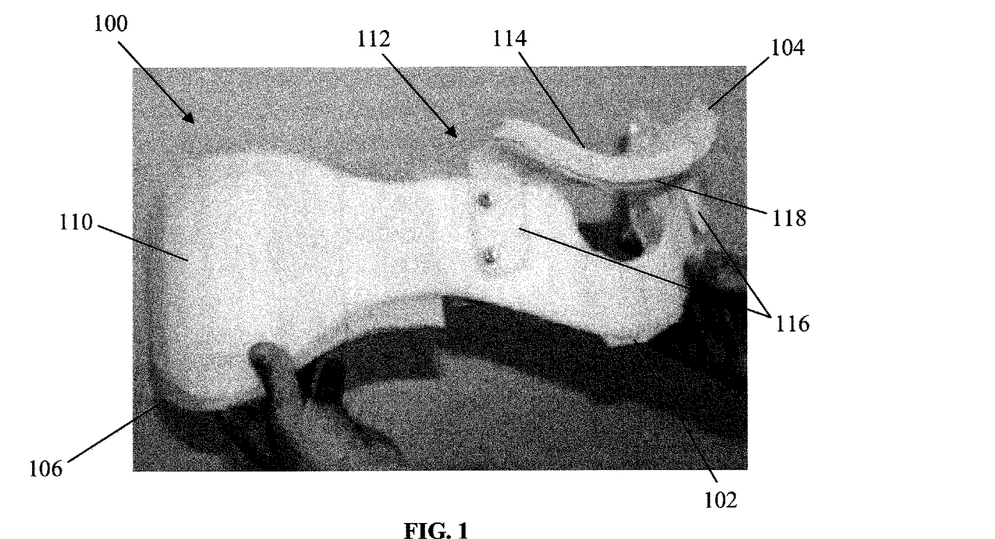
FIGS. 1 and 2 are exterior and interior views of a cervical collar incorporating a cooling device in accordance with aspects of the innovation.
Figure 2:
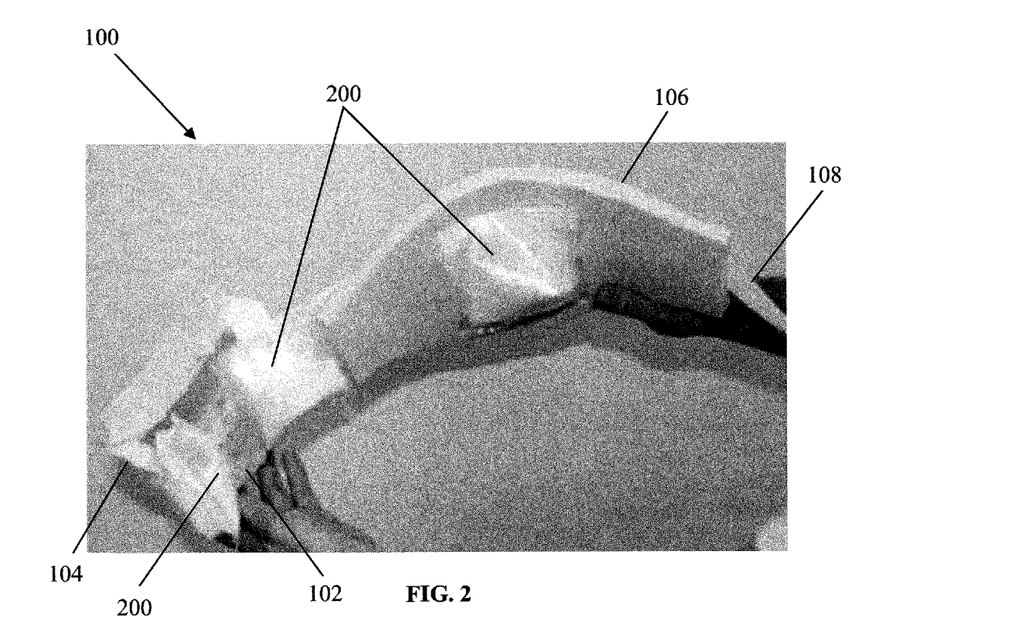

Referring now to the figures, FIGS. 1 and 2 illustrate an example embodiment of a stabilizing device, such as a cervical collar 100 that includes a cooling device in accordance with aspects of the innovation. The cervical collar 100 is most often used to immobilize one's neck in a trauma situation. The cervical collar 100 includes a front portion 102, an optional support 104 for supporting a patient's chin attached to the front portion 102, a back portion 106, and a fastening device 108 such as a strap. The fastening device 108 is attached to one side of the back portion 106 and extends toward the front portion 102. When the patient is wearing the cervical collar 100, the fastening device 108 removably attaches one side of the front portion 102 to thereby couple the front portion 102 to the back portion 106. The fastening device 108 may be any type of device, such as but not limited to a strap that employs a Velcrou-type fastener, snaps, buttons, hooks, etc. It is to be appreciated that most any means for attachment and/or adjustment can be employed in accordance with other aspects of the innovation. It is to be further appreciated that the fastening device 108 is adjustable to allow the cervical collar 100 to conform to patients having different sized necks.

The front and back portion 102, 106 are both made from a soft foam material that can be bent to conform to with the patient's neck, back, and shoulders. It is to be appreciated, however, that the front and back portion 102, 106 can be made from any suitable material as long as it conforms to the patient's neck, such as but not limited to, natural and synthetic polymers, carbon-reinforced materials, metal wire reinforced materials, etc.

Referring specifically to FIG. 1, a flexible integrated outer shell 110 is attached to both the back portion 106 and the front portion 102 thereby coupling the other side of the front portion 102 to the other side of the back portion 106. The outer shell 110 can be attached to the front and back portion 102, 106 via any suitable means, such as but not limited to, an adhesive, rivets, etc. The outer shell 110 is flexible in a horizontal direction thus, allowing the cervical collar 100 to attach around the patient's neck. The outer shell 110, however, is more rigid in the vertical direction thus, giving the cervical collar its stabilization characteristics. The outer shell 110 can be any suitable rigid material, such as but not limited to a molded plastic (e.g., polyethylene, polystyrene, etc.).

Still referring to FIG. 1, the support 104 for supporting the patient's chin, also referred to as a chin cup, is attached to the front portion 102. It is to be appreciated that the support 104 is an optional device and the cervical collar 100 can still perform its intended function in accordance with aspects of the innovation without employing the support 104. The support 104 is disposed beneath the patient's chin for cervical support. The support 104 includes an attachment piece 112 that attaches to the front portion 102 and a rest piece 114. The attachment piece 112 includes two leg members 116 and a curved portion 118 connecting the two leg members 116. The leg members 116 are attached, via rivets or any other suitable means, to the front portion 102 to secure the support 104 to the cervical collar 100. The rest piece 114 is attached, via an adhesive or any other suitable means, to the curved portion 118 to support the patient's chin.

The support 104 can be fixedly attached or adjustably attached to the cervical collar 100. It is understood that individuals have different size necks and chins. Thus, in accordance with aspects of the innovation, the support 104 can be height (or otherwise) adjustable or interchangeable to facilitate comfort and enhanced immobilization effect. For example, in accordance with aspects of the innovation, the support 104 can be adjusted using a tongue and groove mechanism, where the support 104 can act like a tongue and the cervical collar 100 can employ the associated grooves. In accordance with other aspects of the innovation, the support 104 can include preselected heights. For example, a spring-button can be used that catches within a hole in the cervical collar 100 to secure the support 104 at a pre-selected height position. It is to be appreciated that other aspects can employ grooves, hardware (e.g., wing-nuts), etc. for adjustment without departing from the scope of the innovation. Thus, the adjustability of the support 104 and the cervical collar 100, via the fastening device 108, provides a universal fit and applicability of the innovation. Therefore, the cervical collar 100 is adjustable for both length (e.g., support 104) as well as width (e.g., fastening device 108).

In the examples illustrated below, the cervical collar 100 further includes a cooling device that may be in the form of a cooling pack (e.g., chemical pack) integrated into the cervical collar 100, a retainer to receive and hold a cooling pack (e.g., chemical pack, ice pack, sterile water cooling pack, etc.), or a fluid cooling mechanism to allow cooling fluid to be pumped through essential portions of the cervical collar 100.

FIG. 2 illustrates one example embodiment of the cooling device in accordance with aspects of the innovation. The cooling device in this embodiment is a cooling pack 200 that can be either integrated into the cervical collar 100 or can be inserted into a retaining device described below. The cooling pack 200 can be strategically disposed at essential locations on the cervical collar 100 to target the areas of the neck described above. For example, one or more cooling packs 200 can be located on the front portion 102 to target the carotid arteries. In addition, one or more cooling packs 200 can be located on the back portion 106 to target the spinal cord area. The cooling pack 200 can be any type of cooling pack, such as but not limited to chemical pack (e.g., granule-activation packets that when activated releases a cooling agent to provide the desired cooling effect). For example, the granule-activation packets use ammonium nitrate and water. When a user strikes the cooling pack 200 with the palm of a hand, a prescribed amount of water will mix with the ammonium nitrate thereby creating a cold compress. Once the cooling packs 200 are activated, the cervical collar 100 can be placed on the patient to provide the desired therapeutic hypothermia to essential portions of the neck area described above.

The retaining device receives and holds a cooling pack, such as but not limited to, an ice pack or a chemical pack as described above. The retaining device can be strategically disposed at essentials locations on the cervical collar 100 to target the areas of the neck described above. For example, one or more retaining devices can be located on an interior side of the front portion 102 to target the carotid arteries. In addition, one or more retainers can be located on an interior side of the back portion 106 to target the spinal cord area. The retaining device can be in the form of a pocket, a pouch, straps, etc. and can be made from any suitable material, such as but not limited to, plastic, a mesh like material, etc. that sufficiently conducts the cooling effects of the cooling pack. It is to be appreciated that the options for the type and material of the retaining device are limitless and as such all of which are included in the scope of the innovation.

Figure 3:
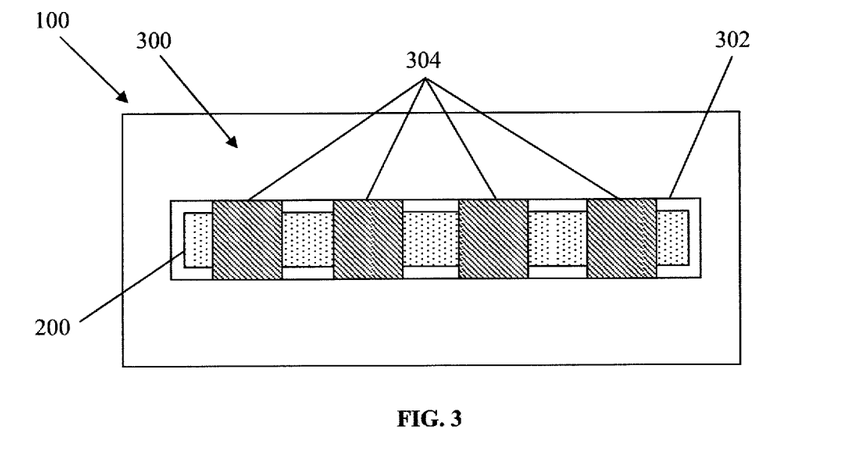
FIG. 3 is a block type diagram of the cervical collar of FIGS. 1 and 2 incorporating an example embodiment of the cooling device in accordance with aspects of the innovation.

For example, FIG. 3 is a block diagram illustration of the cervical collar 100 described above incorporating an example retaining device 300 in accordance with aspects of the innovation. The retaining device 300 includes a channel 302 and one or more covers 304 to hold the cooling pack 200 described above in place. The cover 304 may be made from any material that sufficiently conducts the cooling effects of the cooling pack 200 and that does not irritate the patient's skin. Further, the cover 304 can be a single piece or multiple pieces. In this embodiment, the cervical collar 100 can be packaged and transported in a flat condition to save space in transport vehicles such as emergency medical vehicles. When emergency personnel require the use of the cervical collar 100, the cooling pack 200 can be inserted or slid into the channel 302 and placed on the patient. When the cervical collar 100 is placed on the patient, the cooling pack 200 will activate thereby providing the required cooling effect. It is to be appreciated that the cooling pack 200 can be integrated into the channel 302 thus, saving the emergency personnel the time of placing the cooling pack into the channel 302. Once the cooling packs are secured by the one or more retaining devices, the cervical collar 100 can be placed on the patient to provide the desired therapeutic hypothermia to essential portions of the neck area described above.

Figure 4:
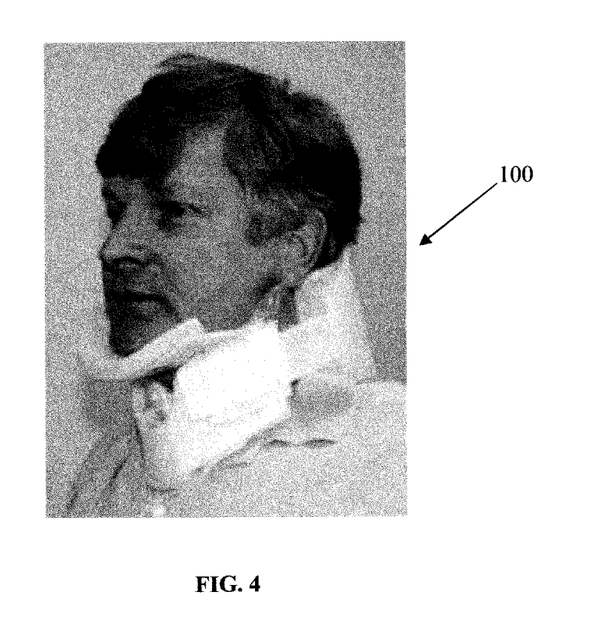
FIG. 4 is a perspective view showing the cervical collar of FIGS. 1 and 2 fitted to the patient in accordance with aspects of the innovation.

For example, FIG. 4 illustrates a perspective view of the cervical collar 100 described above fitted on a patient. As illustrated, the cervical collar 100 has the ability to provide therapeutic hypothermia upon vascular regions to facilitate promptly treating a patient and to minimize risk of further injury than that of conventional cervical collars.

FIGS. 5-8 represent another example embodiment of a cervical collar 500 (hereinafter "collar") incorporating a cooling device. In this embodiment, the cooling device allows cooling fluid from an external cooling system or source to be pumped into and/or circulated through essential portions of the collar 500. The collar 500 includes an outer shell 502, an adjustable support (not shown), and a fluid cooling mechanism 506. It is to be appreciated that while the collar 500 can be used for inducing hypothermia, the collar 500 can also be used as a standard cervical collar when a patient does not require therapeutic hypothermia.

Figure 6:
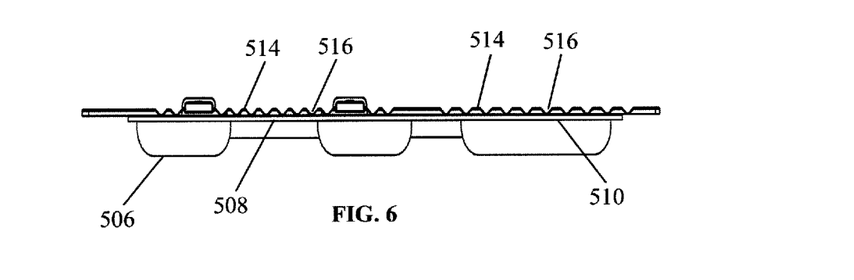
FIG. 6 is a top view of the cervical collar of FIG. 5 in accordance with aspects of the innovation.
Figure 7:
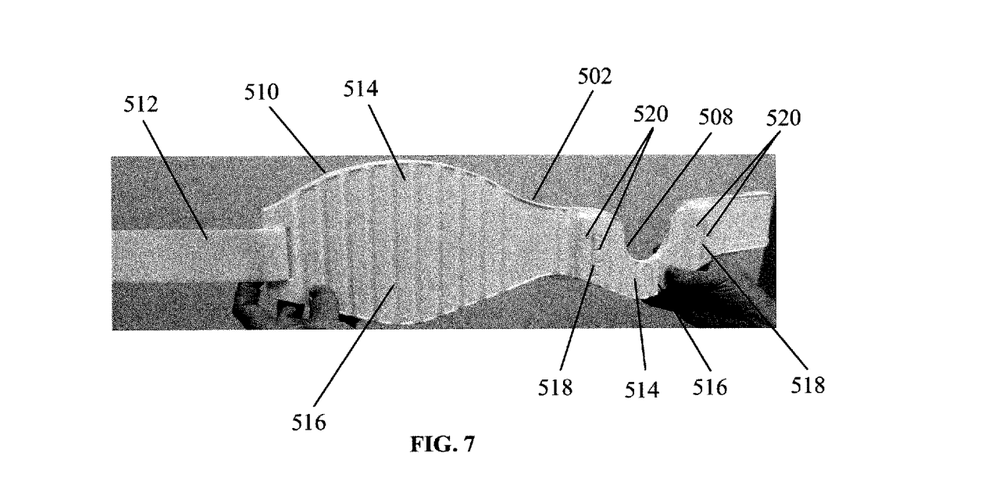
FIG. 7 is a rear view of the cervical collar of FIG. 5 in accordance with aspects of the innovation.

Referring to FIGS. 6 and 7, the outer shell 502 includes a front portion 508 fixedly coupled to a back portion 510 on one side and a fastening device 512 attached to the back portion 510 and removably coupling the front and back portions 508, 510 on an opposite side. The features of the fastening device 512 are similar to the fastening device 108 described above and, as such, will not be repeated.

The outer shell 502 is made from a flexible plastic material, such as but not limited to polyethylene, polystyrene, etc. Further, both the front and back portions 508, 510 include multiple panels 514 each connected by hinged portions 516 that further facilitate in the flexibility of the outer shell 502. This configuration allows EMT personnel to control the flexibility of the collar 500 and easily adjust the collar 500 to fit the patient. In addition, the flexibility characteristic allows the collar 500 to be packaged in a flat state thereby optimizing volume space for shipping and/or storage purposes. The front portion 508 of the outer shell 502 further includes multiple slots 518 and multiple recesses 520 disposed on each side of each slot 518. The multiple slots 518 and multiple recesses 520 facilitate attachment and adjustment of the support to the collar 500 subsequently described.

The support is used to support the patient's chin and is adjustable to conform to the patient similar to the support 104 described above. The support includes attachment legs that attach the support to the front portion 508 and a connection part connecting distal ends of the attachment legs. The connection part serves to support the patient's chin. Multiple slots 518 are defined in the front portion 508 to receive the attachment legs to thereby connect the support to the collar 500. The support can be adjusted by sliding each attachment leg in each slot 518 to a desired position. The attachment legs engage recesses 520 defined on each side of each slot 518 to lock the support in its desired position.

As mentioned above, the connection part provides a connection between the distal ends of the attachment legs. The connection point between the attachment legs and the connection part is hinged to facilitate packaging. Specifically, when the collar 500 is packaged in a flat state, mentioned above, one attachment leg is disconnected from the collar 500 and laid in a flat state. This is possible because of the hinged connection.

Figure 8:
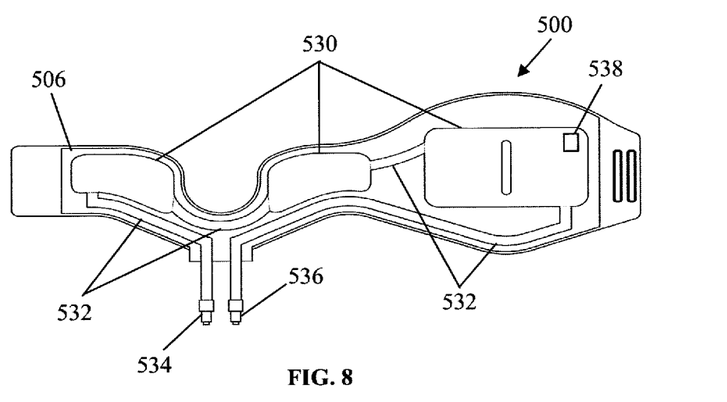
FIG. 8 is a front view of the cervical collar of FIG. 5 in accordance with aspects of the innovation.

Referring to FIG. 8, the fluid cooling mechanism 506 is a single piece bladder type device that includes multiple cooling chambers (or reservoirs) 530, multiple passageways 532, an inlet port 534, and an outlet port 536. The passageways 532 provide a fluid connection between the chambers 530 and the inlet port 534, between the chambers 530 and the outlet port 536, and between the chambers 530 themselves.

The bladder 506 is made from two sheets of a flexible material that is conducive to conducting the cooling effects of the cooling, such as but not limited to, polyethylene. The bladder 506 attaches to an interior portion of the outer shell 502. The bladder 506 may be attached to the interior portion of the outer shell 502 by any suitable means, such as but not limited an adhesive.

The chambers 530 are an integral part of the bladder 506. Specifically, to form the chambers 530, the two flexible sheets are placed in a heat mold and hermetically sealed in an area surrounding the desired location of each chamber 530. The innovation is not dependent on the number of chambers 530 formed in the bladder 506. It is to be appreciated, however, that the number and location of the chambers 530 targets essential areas of the patient's neck (e.g., carotid arteries, spinal area, etc.). For example, in the embodiment shown in FIG, 8, the number of chambers 530 is three to target the carotid arteries and the spinal area.

As mentioned above, the passageways 532 provide a connection between the chambers 530, and between the chambers 530 and the inlet and outlet ports 534, 536. The passageways 532 may be comprised of embedded tubes or may be integrally formed in the bladder 506. Specifically, multiples tubes can be positioned at proper locations in the bladder 506 during formation of the chambers 530 described above, thus, embedding the tubes in the bladder 506. The passageways 532 may also be integrally formed in the bladder 506 by hermetically sealing an area surrounding each passageway 532 similar to the formation of the chambers 530 described above.

The inlet and outlet ports 534, 536 provide a connection between the bladder 506 and the external cooling system or source. The connection between the bladder 506 and the external cooling system or source can be any suitable mechanical connection device, such as but not limited to, quick couplers, a screw type device, etc. Further, the inlet and outlet ports 534, 536 may include a valve to regulate the flow of cooling fluid into and/or out of the bladder 506. It is to be appreciated that the inlet port 534 and the outlet port 536 can be switched. In other words, the inlet port 534 can serve as the outlet port 536 and the outlet port 536 can serve as the inlet port 534.

Figures 9, 10, 11:
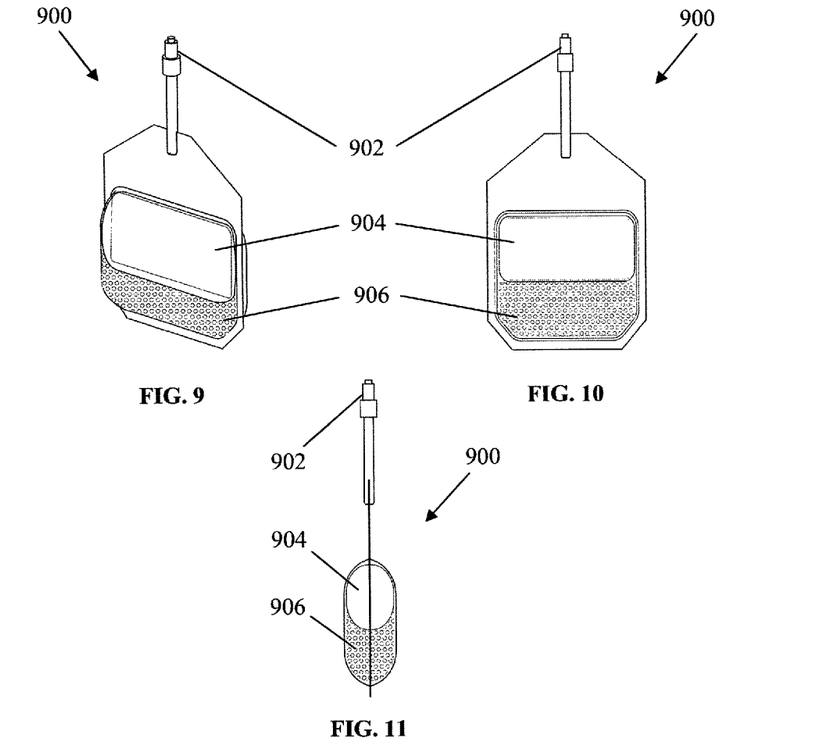
FIGS. 9-11 are perspective, front and side views respectively of a cooling source in accordance with aspects of the innovation.

One such example of a cooling source is a cooling pack 900 illustrated in FIGS. 9-11. The cooling pack 900 includes a port 902 that acts as both an inlet port and an outlet port. The cooling pack 900 is a granule-activation packet that uses a fluid 904, such as but not limited to, water and a chemical 906, such as but not limited to, ammonium nitrate that when mixed together create a cooling fluid. When a user strikes the cooling pack 900 with the palm of their hand, a prescribed amount of water will mix with the ammonium nitrate thereby creating a cooling fluid. The cooling fluid from the cooling pack 900 can then be pumped into the bladder 506 via the inlet port 534 and into each chamber 530 via the passageways 532, as described below. In addition, once the cooling fluid inside the bladder 506 begins to warm, the empty cooling pack 900 can be attached to the outlet port 536 and a new cooling pack 900 can be attached to the inlet port 534. The cooling fluid from the new cooling pack 900 can then be pumped into the bladder 506 thereby forcing the warm fluid out of the bladder 506 through the outlet port 536 and back into the original cooling pack 900. Thus, cooling fluid can essentially be continuously pumped through the collar 506 by EMT personnel who do not have access to a continuous external cooling system (described below) in the field.

In conjunction with the cooling packs 200, 900 previously described, the cervical collar 500 may include an indicator 538 (see FIG. 8) disposed on the retaining device 300 or on the bladder 506 (e.g., on at least one chamber 530 and/or at least one passageway 532) that indicates an approximate body temperature of the patient and/or an approximate temperature of the cooling fluid in the cooling pack 200, 900. In one example, the indicator 538 can change color based on the temperature of the cooling fluid. For example, the indicator 538 may be a first color (e.g., blue, dark blue, etc.) when the temperature of the cooling fluid is at a temperature that provides adequate cooling to the patient. As the temperature of the cooling fluid begins to lose its cooling effect (e.g., the cooling fluid begins to warm), the indicator 538 may turn a second color (e.g., orange). As the temperature of cooling fluid continues to warm (e.g., approaches ambient temperature), the indicator 538 may turn a third color (e.g., red) indicating that the cooling fluid is no longer providing adequate cooling to the patient. The indicator 538 can provide a quick visual means for the EMT personnel to determine if the cooling pack 200 should be replaced or if additional cooling fluid should be pumped into bladder 506 with another cooling pack 900.

In another example embodiment, the bladder 506 may act as the indicator. For example, the bladder 506 may be made from a material that changes color based on temperature, as previously described.

In another example embodiment, the outer shell 502 may be made from a transparent material or may include a viewing window that permits the EMT personnel to view the patient's neck for signs of trauma and/or view the indicator 538 described above.

As mentioned above, the collar 500 can be connected to an external cooling system that can continuously pump a cooling fluid through the bladder 506 thereby providing a constant circulation of cooling fluid. In addition, a temperature of the cooling fluid can be regulated to maintain a predetermined temperature or adjust the temperature as desired. As such, this embodiment can be used to perform therapeutic hypothermia over an extended period of time to treat a particular type of injury or perform a particular type of procedure. For example, this example embodiment, as well as those described above, can be in the form of a wrap that employs the bladder 506 to treat injuries to the arms, shoulder, legs, knees, etc., as well as the neck area, where therapeutic hypothermia is required over an extended period of time.

Figure 12:
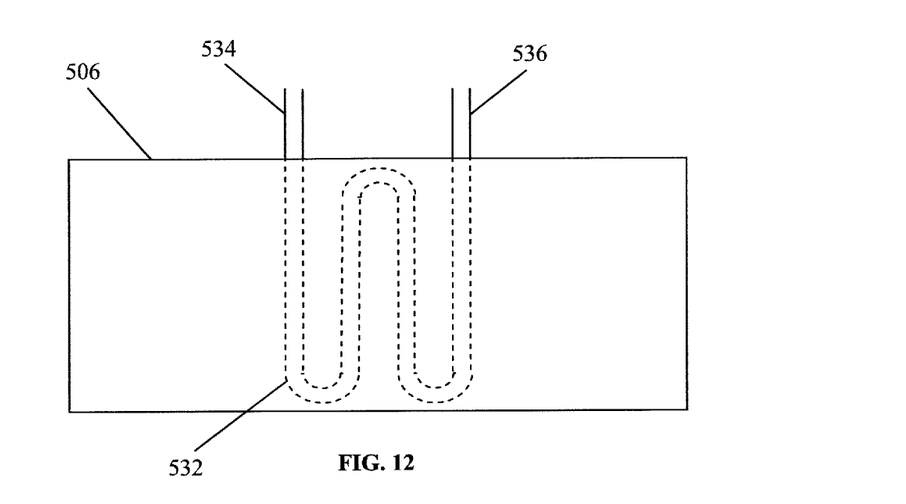
FIG. 12 is a block type diagram of another embodiment of a cervical collar incorporating a cooling device in accordance with aspects of the innovation.

It is to be appreciated that the bladder 506 can be modified to exclude the chambers and simply include passageways 532 that run through the bladder 506 in desired locations, as shown in FIG. 12. The passageways 532 would connect to both the inlet and outlet ports 534, 536 to allow the continuous circulation of cooling fluid, as described above.

Figure 5:
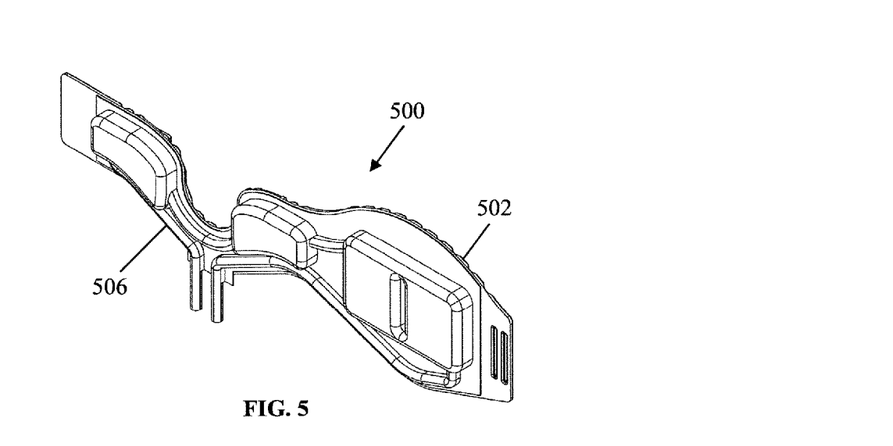
FIG. 5 is a perspective view of another embodiment of a cervical collar incorporating a cooling device in accordance with aspects of the innovation.
Figure 13:
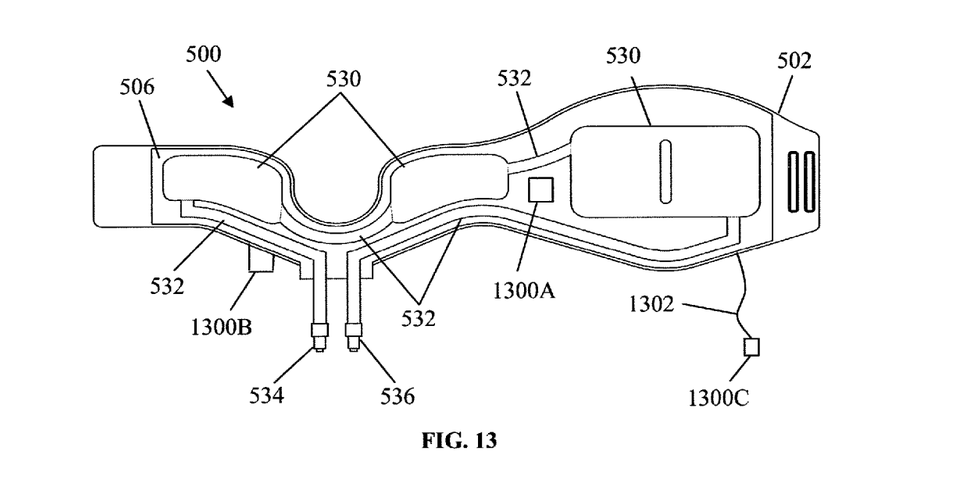
FIG. 13 is a front view of the cervical collar of FIG. 5 incorporating a temperature sensing device in accordance with an aspect of the innovation.

Referring to FIG. 13, the example embodiment of the cervical collar 500 illustrated in FIG. 5 above may include a temperature sensor 1300A or 1300B or 1300C that measures a body temperature of the patient. Although like features are referenced in FIG. 13, a description of such features will not be repeated for simplicity. The temperature sensors 1300A-C illustrated in FIG. 13 can be any type of temperature sensor, such as but not limited to, an infrared sensor, a stick tab sensor, etc. The presence of a temperature sensor allows medical personal to not only monitor, but also regulate the patient's body temperature via the external cooling system mentioned above. Thus, to increase or decrease the body temperature of the patient, the flow rate of the external cooling system is either increased or decreased respectively (alternatively, the temperature of the cooling can be adjusted as opposed to the flow rate). Thus, medical personal are able to maintain the patient's body temperature at a target temperature to thereby minimize the traumatic effect to the patient. It is to be understood, that any type of sensor that measures a physical characteristic of the patient may be included in the cervical collar. For example, in lieu of or in addition to a temperature sensor, a sensor may be included that measures the patient's pulse, etc.

Although there are multiple temperature sensors illustrated in FIG. 13, it is to be understood that only one temperature sensor is required. Multiple temperature sensors are shown in FIG. 13 to illustrate that the temperature sensor can be arranged with the cervical collar 500 in several different configurations.

For example, in one embodiment, temperature sensor 1300A can be disposed on the bladder 506 such that when the cervical collar 500 is placed on the patient, the temperature sensor 1300A is already positioned to monitor the body temperature of the patient.

In another example embodiment, temperature sensor 1300B can have a tab like configuration that attaches to a bottom edge 542 (as shown in FIG. 13) of the cervical collar 500. Thus, when the cervical collar 500 is placed on the patient, the temperature sensor 1300B is already positioned to monitor the body temperature of the patient. It is to be appreciated that the tab like temperature sensor 1300B can attach to a top or side edge of the cervical collar 500.

In still yet another example embodiment, the temperature sensor can be attached to any location (e.g., the outer shell 502, the bladder 506, etc.) on the cervical collar 500 via a tether 1302, as illustrated by temperature sensor 1300C. Once the cervical collar 500 is in place the temperature sensor 1300C can be placed on the patient at any convenient location, such as but not limited to, the forehead, neck area, etc.

Figure 14:
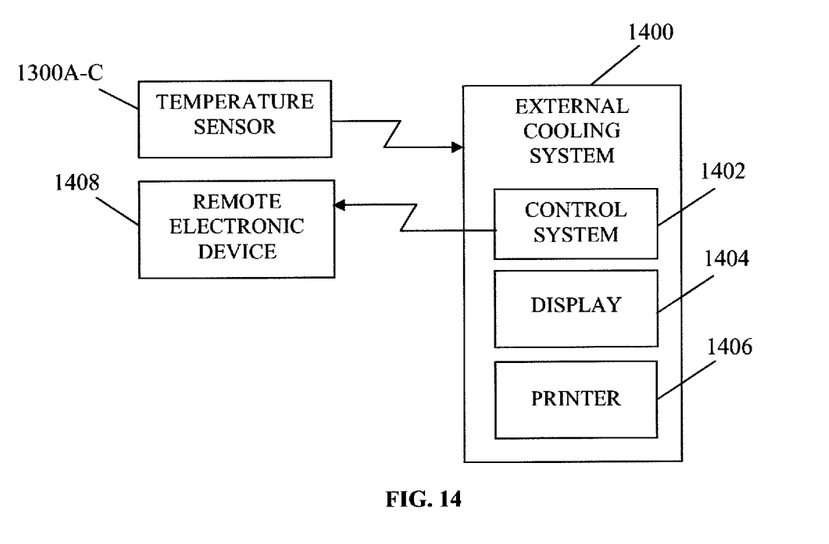
FIG. 14 is a block diagram illustration of an external cooling system in accordance with an aspect of the innovation.

Referring to FIG. 14, in another embodiment, the temperature sensor 1300A-C can communicate with the external cooling system 1400 to automatically control the flow rate of the cooling fluid, thereby automatically adjusting the body temperature of the patient. For example, the body temperature of the patient can be continuously transmitted to a control system 1402 of the external cooling system 1400. The control system 1402 can then adjust the flow rate of the cooling fluid to adjust the body temperature until a desired target body temperature is reached. Further, the control system 1402 can continually or incrementally adjust the flow rate of the cooling fluid to gradually increase or decrease the patient's body temperature as desired.

In another example embodiment, the control system 1402 can be programmed to automatically adjust the flow rate of the cooling fluid to reach a target temperature based on several factors, including but not limited to, the patient's characteristics (e.g., the patient's health history if available, the patients physical make-up (e.g., height, weight, etc.)), environmental conditions (e.g., ambient temperature, etc.), etc.

Still referring to FIG. 14, patient information, such as but not limited to, patient's body temperature, flow rate of cooling fluid, patient's pulse, etc., may be visually displayed via a display 1404 associated with the external cooling system or printed via a printer 1406 associated with the external cooling system 1402. Further, the information may be transmitted from the control system 1402 to a remote location (e.g., medical facility) or to an electronic device 1408, such as but not limited to, a mobile phone, a tablet, a PDA, a computer, etc.

Figure 15:
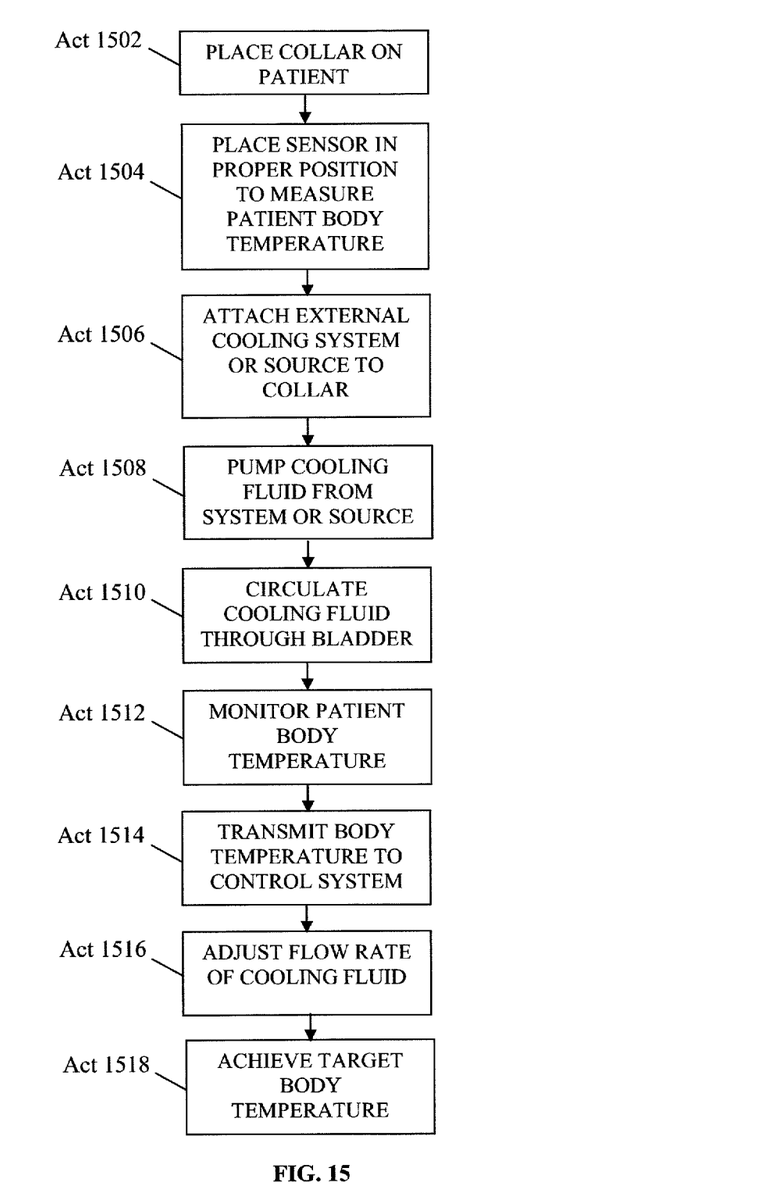
FIG. 15 illustrates a method of operating the cervical collar of FIG. 13 in accordance with aspects of the innovation.
Figure 16:
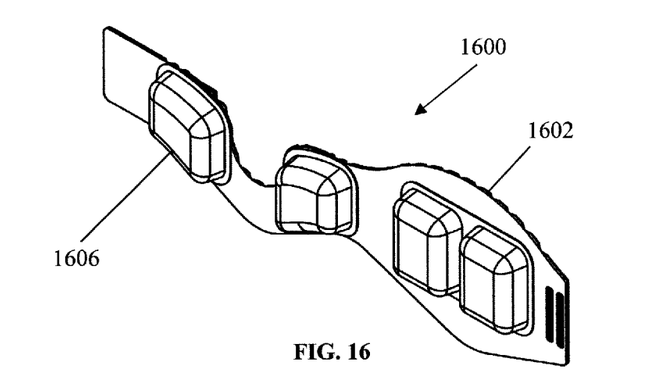
FIG. 16 is a perspective view of another embodiment of a cervical collar incorporating a cooling device in accordance with aspects of the innovation.

Referring to FIG. 15, a method of using the collar 500 incorporating the fluid cooling mechanism 506 will now be described. At Act 1502, the collar 500 is placed on the patient. At Act 1504, the sensor is properly placed to monitor the patient's temperature. At Act 1506, the external cooling system or source is connected to the bladder via the inlet and outlet ports 534, 536. At Act 1508, cooling fluid from the external cooling system or source is pumped into the bladder 506. If desired, at Act 1510, the cooling fluid can be continuously circulated through the bladder 506. At Act, 1512 the patient's body temperature is monitored. At Act 1514, the body temperature is transmitted to the control system. At Act 1516, the flow rate of the cooling fluid is adjusted to regulate the patient's body temperature. At Act 1518, the target body temperature is achieved.

FIGS. 16-19 represent another example embodiment of a cervical collar 1600 (hereinafter "collar") incorporating a cooling device. The collar 1600 includes an outer shell 1602, an adjustable support (not shown), and a cooling device 1606. It is to be appreciated that while the collar 1600 can be used for inducing hypothermia, the collar 1600 can also be used as a standard cervical collar when a patient does not require therapeutic hypothermia.

Figure 17:
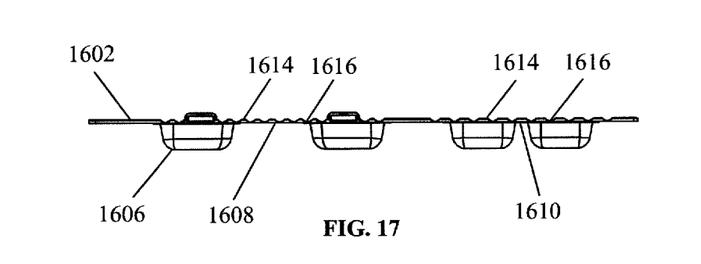
FIG. 17 is a top view of the cervical collar of FIG. 16 in accordance with aspects of the innovation.
Figure 18:
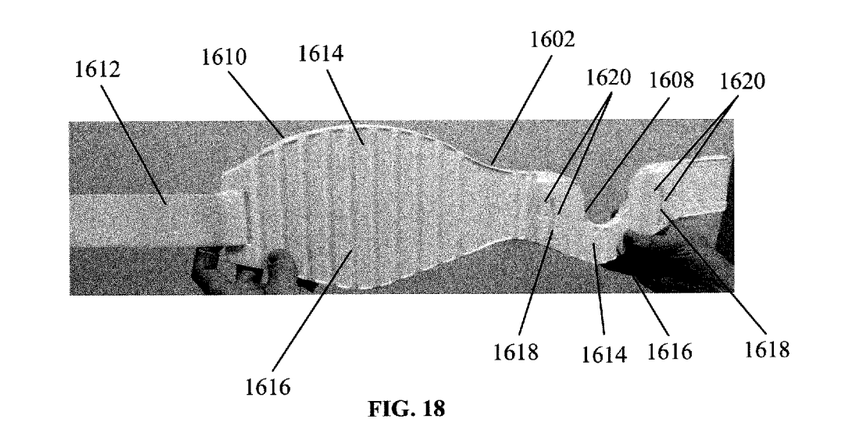
FIG. 18 is a rear view of the cervical collar of FIG. 16 in accordance with aspects of the innovation.

Referring to FIGS. 17 and 18, the outer shell 1602 includes a front portion 1608 fixedly coupled to a back portion 1610 on one side and a fastening device 1612 attached to the back portion 1610 and removably coupling the front and back portions 1608, 1610 on an opposite side. The features of the fastening device 1612 are similar to the fastening device 108 described above and, as such, will not be repeated.

The outer shell 1602 is made from a flexible plastic material, such as but not limited to polyethylene, polystyrene, etc. Further, both the front and back portions 1608, 1610 include multiple panels 1614 each connected by hinged portions 1616 that further facilitate in the flexibility of the outer shell 1602. This configuration allows EMT personnel to control the flexibility of the collar 1600 and easily adjust the collar 1600 to fit the patient. In addition, the flexibility characteristic allows the collar 1600 to be packaged in a flat state thereby optimizing volume space for shipping and/or storage purposes. The front portion 1608 of the outer shell 1602 further includes multiple slots 1618 and multiple recesses 1620 disposed on each side of each slot 1618. The multiple slots 1618 and multiple recesses 1620 facilitate attachment and adjustment of the support to the collar 1600 subsequently described.

The support is used to support the patient's chin and is adjustable to conform to the patient. The support includes attachment legs that attach the support to the front portion 1608 and a connection part connecting distal ends of the attachment legs. The connection part serves to support the patient's chin. Multiple slots 1618 are defined in the front portion 1608 to receive the attachment legs to thereby connect the support to the collar 1600. The support can be adjusted by sliding each attachment leg in each slot 1618 to a desired position. The attachment legs engage recesses 1620 defined on each side of each slot 1618 to lock the support in its desired position.

As mentioned above, the connection part provides a connection between the distal ends of the attachment legs. The connection point between the attachment legs and the connection part is hinged to facilitate packaging. Specifically, when the collar 1600 is packaged in a flat state, mentioned above, one attachment leg is disconnected from the collar 1600 and laid in a flat state. This is possible because of the hinged connection.

Figure 19:
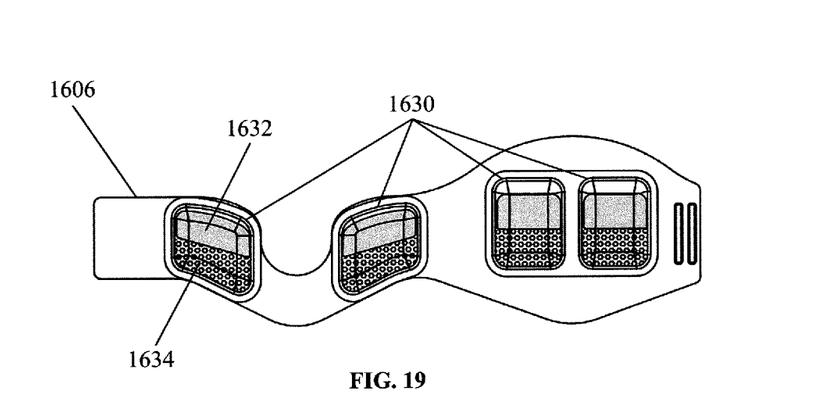
FIG. 19 is a front view of the cervical collar of FIG. 16 in accordance with aspects of the innovation.

Referring to FIG. 19, the cooling device 1606 includes one or more cooling packs 1630 integrated into an interior of the collar 1600. The cooling pack(s) 1630 can be strategically disposed at essential locations on the cervical collar 1600 to target the areas of the neck described above. For example, the cooling pack(s) 1630 can be located on the front portion 1608 to target the carotid arteries and/or on the back portion 1610 to target the spinal cord area. The cooling pack(s) 1630 can be any type of cooling pack, such as but not limited to chemical pack. For example, the cooling pack(s) 1630 can be a granule-activation packet uses a fluid 1632, such as but not limited to, water and a chemical 1634, such as but not limited to, ammonium nitrate that when mixed together create a cooling fluid. Once the cooling packs 1630 are activated, the cervical collar 1600 can be placed on the patient to provide the desired therapeutic hypothermia to essential portions of the neck area described above.

In other embodiments, the cervical collar disclosed herein can include a marking(s) and/or be made from different colors where the markings and/or colors represent a particular attribute. For example, the marking(s) and/or color may represent a type of injury that the cervical collar should be used on, a size of the cervical collar, a cooling fluid flow rate, if the cervical collar is used as a cooling device (e.g., the color blue) or used as a warming device (e.g., the color red), etc. In addition, the cervical collar may include multiple markings or different parts of the cervical collar may be made of different colors where certain combinations of markings and/or colors (e.g., the bladder may be one color and the outer shell may be a different color) represent one or more attributes of the cervical collar, such as those listed above.

For example, as mentioned above, the cervical collar can selectively cool the cerebral vasculature relative to the whole body. Thus, the cervical collar may include markings and/or be color coded to indicate that the cervical collar can be used to electively cool the cerebral vasculature. As medical professionals have a number of medical devices at their disposal, such as neck braces or other traditional cervical collars, the innovative cervical collar that includes markings and/or is color coded provides the medical professionals a vehicle to quickly identify the proper medical device required to treat the patient in circumstances where time is of the utmost importance.

As noted above, the innovation disclosed herein is not limited to a cervical collar to treat the neck area of a person. The innovation can be applied to any portion of the body that requires therapeutic hypothermia treatments. Thus, while a particular type of cooling device is described and illustrated, it is to be understood that alternative aspects can employ the cooling device without departing from the spirit and/or scope of the innovation.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A cervical collar that facilitates therapeutic hypothermia comprising:
   an outer shell having a front portion and a back portion fixedly coupled to the front portion on one side and removably coupled to the front portion on an opposite side;
   a fastening device that removably couples the back portion to the front portion on the opposite side;
   a bladder having at least one cooling device that holds cooling fluid disposed on an interior of the outer shelf;
   a sensor that measures a physical characteristic of the patient; and
   an indicator that measures a temperature of the cooling fluid and that changes color based on the measured temperature,
   wherein the indicator is the bladder, and
   wherein the at least one cooling device is disposed on an anterior portion and on a posterior portion of a patient's neck area to thereby selectively induce hypothermia in a cerebral vasculature of the patient.

2. The cervical collar of claim 1, wherein the sensor is a temperature sensor that measures a body temperature of the patient.

3. The cervical collar of claim 2, wherein the temperature sensor is disposed on the bladder such that the temperature sensor is positioned to monitor the body temperature of the patient when the cervical collar is placed on the patient.

4. The cervical collar of claim 2, wherein the temperature sensor is attached to the outer shell with a tether.

5. The cervical collar of claim 2, wherein the at least one cooling device includes a fluid cooling mechanism attached to the interior of the cervical collar, and wherein the fluid cooling mechanism receives and circulates a cooling fluid from an external cooling system.

6. The cervical collar of claim 5, wherein the temperature sensor communicates with the external cooling system to automatically control a flow rate of the cooling fluid to regulate the patient's body temperature.

7. The cervical collar of claim 6, further comprising a control system that automatically controls the flow rate of the cooling fluid based on at least one of a target body temperature, patient characteristics, and environmental conditions.

8. The cervical collar of claim 7, wherein the external cooling system includes a display that displays patient information.

9. The cervical collar of claim 7, wherein the external cooling system communicates with a remote location and/or a device thereby providing patient information to the remote location and/or the device.

10. The cervical collar of claim 2, wherein the at least one cooling device includes a plurality of chambers configured to hold the cooling fluid, a plurality of passageways, an inlet port, and an outlet port, wherein the passageways provide a fluid connection between the plurality of chambers and the inlet and outlet ports, and between the plurality of chambers, and wherein the inlet and outlet ports provide a connection between the passageways and the external cooling system or source.

11. The cervical collar of claim 2, wherein both the front portion and the back portion includes a plurality of panels and hinged portions connecting the plurality of panels to facilitate flexibility of the cervical collar.

12. The cervical collar of claim 11 further comprising a support removably attached to the front portion to support and immobilize the patient's chin, wherein the support is a fixed support or an adjustable support that adapts to a configuration of the patient, wherein the support includes hinged portions and can be partially disconnected from the front portion and laid in a flat state to facilitate packaging of the cervical collar in a flat state.

13. The cervical collar of claim 1 further comprising markings and/or color coded parts that identify an attribute of the cervical collar.

14. The cervical collar of claim 1, wherein the cooling chamber cools a carotid artery in the patient.

15. A cervical collar comprising:
an outer shell;
a fastening device that removably couples opposite ends of the outer shell;
a bladder having at least one cooling chamber configured to hold a cooling fluid disposed on an interior of the outer shell; and
an indicator that measures a temperature of the cooling fluid,
wherein the indicator is the bladder, and
wherein the bladder changes color based on the temperature of the cooling fluid in the at least one cooling chamber.

16. The cervical collar of claim 15 further comprising an inlet port and an outlet port that provide a fluid connection between at least one passageway and an external cooling source.

17. The cervical collar of claim 15, wherein the indicator is a first color when the cooling fluid is at a temperature that provides adequate cooling.

18. The cervical collar of claim 17, wherein the indicator is a second color when the cooling fluid begins to lose its cooling effect.

19. The cervical collar of claim 18, wherein the indicator is a third color when the temperature of the cooling fluid is such that the cooling fluid no longer provides adequate cooling to the patient.

* * * * *